United States Patent
Hardcastel, III

(12) 
(10) Patent No.: US 6,659,638 B1
(45) Date of Patent: Dec. 9, 2003

(54) DYNAMIC TEMPERATURE CONTROLLED ACCELERATED WEATHERING TEST APPARATUS

(75) Inventor: Henry K. Hardcastel, III, Sunrise, FL (US)

(73) Assignee: Atlas Material Testing Technology, L.L.C., Chicago, IL (US)

( * ) Notice: Subject to any disclaimer, the term of this patent is extended or adjusted under 35 U.S.C. 154(b) by 0 days.

(21) Appl. No.: 10/151,577

(22) Filed: May 17, 2002

(51) Int. Cl.[7] .............................................. G01N 17/00
(52) U.S. Cl. ............................ 374/57; 374/5; 73/865.6; 236/49.3
(58) Field of Search .............................. 374/57, 5, 4, 6, 374/7, 45, 138; 73/865.6, 150 R; 356/51; 236/49.1, 49.3, DIG. 9

(56) References Cited

U.S. PATENT DOCUMENTS

| | | | |
|---|---|---|---|
| 2,945,417 A | * 7/1960 | Caryl et al. | 73/150 R |
| 3,501,942 A | 3/1970 | Fitzgerald et al. | 374/57 |
| 4,391,522 A | * 7/1983 | Schmid et al. | 73/150 R |
| 4,704,903 A | 11/1987 | Suga et al. | 73/865.6 |
| 4,734,872 A | 3/1988 | Eager et al. | 374/57 |
| 4,760,748 A | 8/1988 | Katayanagi et al. | 374/57 |
| 4,807,247 A | 2/1989 | Robbins, III | 374/57 |
| 4,817,447 A | * 4/1989 | Kashima et al. | 73/865.6 |
| 4,843,893 A | * 7/1989 | Huber et al. | 73/865.6 |
| 4,957,011 A | 9/1990 | Huber et al. | 374/57 |
| 5,138,892 A | 8/1992 | Suga | 374/57 |
| 5,503,032 A | * 4/1996 | Tikhtman et al. | 73/865.6 |
| 5,646,358 A | 7/1997 | Tikhtman et al. | 73/865.6 |
| 5,854,433 A | 12/1998 | Patel et al. | 73/865.6 |
| 6,023,985 A | 2/2000 | Fournier | 73/865.6 |
| 6,073,500 A | 6/2000 | Jorgensen et al. | 73/865.6 |
| 6,533,452 B1 | * 3/2003 | Hardcastle, III | 374/57 |

FOREIGN PATENT DOCUMENTS

WO   WO 200223164 A1 * 3/2002 .......... G01N/17/00

* cited by examiner

*Primary Examiner*—Diego Gutierrez
*Assistant Examiner*—Stanley J. Pruchnic, Jr.
(74) *Attorney, Agent, or Firm*—Vedder Price Kaufman & Kammholz

(57) ABSTRACT

An accelerated weathering test apparatus for concentrating solar radiation upon at least one test specimen including a target board, a reflector device, an air circulation device, a feedback device, an input device and a controller. Ambient air is circulated over the target board to cool the test specimens. The controller continuously sets a dynamic set point based on the reference signal from the input device which is representative of a complex temperature cycle of a material end-use application and adjusts the rate of air circulation based on a test signal from the feedback device.

26 Claims, 6 Drawing Sheets

DYNAMIC TEMPERATURE CONTROLLED ACCELERATED WEATHERING TEST APPARATUS

FIELD OF THE INVENTION

The present invention relates generally to accelerated weathering test devices of the type used to expose test specimens of exterior coatings such as paints and finishes, as well as fabrics and other materials to solar radiation and other weathering effects on an accelerated basis, and more particularly, to such an accelerated weathering test device adapted to dynamically control a test specimen temperature.

DESCRIPTION OF THE PRIOR ART

Manufacturers of exterior coatings, such as paints and finishes, as well as plastics and other components which tend to degrade under exposure to solar radiation and other weathering effects, often want to know how such products will perform following years of exposure. However, such manufacturers typically require such information in a much shorter time than it would take to expose such materials to weathering effects under normal conditions. Accordingly, accelerated weathering test devices have been developed which accelerate the effects of weathering due to outdoor exposure in a much shorter time so that manufacturers need not actually wait five or ten years in order to determine how their products will hold up after five or ten years of actual outdoor exposure.

One known accelerated weathering test device is disclosed in U.S. Pat. No. 2,945,417, issued to Caryl et al. The aforementioned test device includes a Fresnel-reflecting solar concentrator having a series of ten flat mirrors which focus natural sunlight onto a series of test specimens secured to a target board measuring approximately five (5) inches wide by fifty-five (55) inches long. The Fresnel-reflecting solar concentrator directs solar radiation onto the target board area with an intensity of approximately eight suns. Both the bed which supports the mirrors of the solar concentrator, and the target board, are supported by a frame which can be rotated to follow daily movements of the sun. A solar tracking mechanism responsive to the position of the sun, controls the operation of an electric motor that is used to rotate the test apparatus to follow movements of the sun. The axis of rotation of the test machine is oriented in a north-south direction, with the north elevation having altitude adjustment capability to account for variation in the sun's altitude at various times during the year. Such known testing devices are also provided with an air tunnel mounted above the target board. An air deflector causes air escaping from the air tunnel to be circulated across the test specimens mounted to the target board to prevent the test specimens from overheating due to the concentrated solar radiation to which they are exposed. The amount of air is controlled by the dimension of the gap between the deflector and the specimen. A squirrel cage blower communicates with the air tunnel for blowing cooling ambient air there through. In addition, water spray nozzles are provided proximate to target board for wetting the test samples at periodic intervals to simulate the weathering effects of humidity, dew, rain, etc.

Another known accelerated weathering test device is disclosed in U.S. Pat. No. 4,807,247 issued to Robins, 111. The aforementioned test device includes all the structure previously described above with respect to the '417 patent and further includes a system for maintaining a uniform, constant test specimen temperature during daylight hours despite variations in ambient air temperature and variations in solar radiation intensity.

The system includes a temperature sensor mounted to the target board for exposure to the concentrated solar radiation and for generating an electrical signal indicative of the temperature of the test specimen mounted to the target board. The system further includes a control mechanism electrically coupled to the temperature sensor and responsive to the electrical signal generated thereby for selectively controlling the application of electrical power to the electrical motor included within the air circulation system. In this manner, the control mechanism serves to vary the speed of the electric motor and thereby control the flow rate of cooling ambient air circulating across the target board so that the temperature of the test specimen remains constant at the desired set point.

When the sensed temperature of the test specimen increases, the control mechanism increases the speed of the blower motor to circulate more cooling ambient air across the target board in order to lower the temperature of the test samples back to the desired set point. Similarly, if the sensed temperature of the target samples drops below the desired nominal temperature, the control mechanism decreases the speed of the blower to permit the test samples to warm up back to the desired set point.

The temperature control mechanism also includes a user operable adjustment mechanism, in the form of the control knob, for allowing a user to set a static, desired target specimen temperature. A bypass switch is also provided for allowing the user to operate the test device in the controlled temperature-mode as described above, or in an uncontrolled mode wherein the blower motor operates at a constant speed.

Standardized testing methods have been developed for operating accelerated weathering test devices of the type described above. The American Society for Testing and Materials (ASTM) has issued standards G90, E838, D4141, D3105, D3841, D5105, E1596 and D4364 covering the testing procedures and the operating parameters for conducting such outdoor accelerated weathering tests. Other standards and appraisals have also been developed and specified by the Society of Automotive Engineers (SAE), Ford, International Standards Organization (ISO), American National Standards Institute (ANSI), Japan Industrial Standard (JIS), namely, SAE J576, SAE J1961, Ford EJB-M1J14-A, Ford EST-M5P11-A, ISO 877, ANSI/NSF 54, JIS Z 2381 and MIL-T-22085D.

Apart from outdoor accelerated weathering test devices of the type described above, other test devices are also known which utilize an artificial source of radiation to expose the test specimens. An example of such a test device is disclosed in U.S. Pat. No. 3,664,188 issued to Kockott. While such test devices have the advantage of permitting precise control over radiation intensity, temperature and humidity, such test devices have often failed to duplicate the actual light spectrum of natural sunlight to which the specimens under test will actually be exposed in everyday use. It has been acknowledged and recognized by those of skill in the art that natural sunlight and artificial sunlight test apparatus are distinct from one another and provide different sets of empirical data.

Outdoor accelerated weathering test devices of the type described above in regard to U.S. Pat. Nos. 2,945,417 and 4,807,247, have the advantage of using natural sunlight, and hence the specimens under test are exposed to the actual spectrum of sunlight. However, disadvantages of outdoor accelerated weathering test devices have been discovered.

One such disadvantage is that test results obtained from an outdoor accelerated weathering test apparatus without temperature control are not repeatable or reproducible. The blower motor used to circulate cooling air across the test specimens operates at a constant speed and generates a constant flow rate of cooling across the test specimens. Accordingly, the temperature of the test specimens cannot be controlled and is subject to random constant changes in the local ambient air temperature and solar radiation intensity. Further, it has also been discovered that the changes in the temperature of the test specimens can alter the rate of weathering which occurs. For example, test specimens tend to degrade faster in the summer than in the winter due to nominally higher test specimen temperatures in the summer as a result of both higher average ambient temperature and greater solar radiation intensity. Therefore, in order to obtain repeatable and reproducible test results, the temperature of the test specimens must be controlled.

Another disadvantage is that test results obtained from an outdoor accelerated weathering test apparatus having a static temperature control are not repeatable or reproducible. Further the test specimens are not controlled to reproduce a natural weathering function when the set point is constant. This is a critical disadvantage because the manner in which materials degrade is defined by their end-use application and environment. The test results are better than an uncontrolled apparatus. However, materials in end-use applications encounter temperature fluctuations that are best represented by complex functions. A simple diurnal material temperature cycle is a complex function of ambient temperatures, solar irradiance, material heat capacity, material re-radiance losses, conductive heat losses, convective heat losses, etc. Diurnal cycles are also super imposed upon longer time-scale cycles (season, annual, etc.) as well as intermittent random variables such as intermittent clouds, rain, dew, etc. Prior devices which are uncontrolled or maintain the test specimens at a manually set static temperature, do not account for the above variables. Rather, the temperature control for prior art accelerated weathering test apparatus simply operates at a desired, but static set temperature.

Therefore, there exists a need for a dynamically controlled accelerated weathering test apparatus which overcomes the disadvantages of prior art devices and simulates the complex temperature cycles materials encounter in end-use environments described above.

SUMMARY OF THE INVENTION

One aspect of the present invention is directed to an accelerated weathering test apparatus of the type used to concentrate solar radiation upon target specimens where the apparatus is adapted to dynamically control a target specimen temperature to simulate a complex temperature cycle of a material end-use application. The apparatus includes a target board for supporting at least one test specimen for exposure to concentrated solar radiation. A reflector device reflects solar radiation and concentrates the reflective solar radiation on to the target board for illuminating the at least one test specimen. An air circulation device circulates ambient air over the target board for adjusting the temperature of the at least one test specimen. The air circulation device includes an electric motor and a fan powered by the electric motor for creating a flow of ambient air. A feedback device is mounted to the target board for exposure to the concentrated solar radiation and for generating a test signal responsive to the temperature thereof and representative of the test specimen temperature. An input device generates a dynamic reference signal representative of a complex temperature cycle of a material end-use application. A controller connects to the input device and is responsive to the reference signal for generating a dynamic temperature set point and is further connected to the feedback device and is responsive to the test signal for selectively controlling the application of electrical power to the electric motor in order to control a rate at which ambient air is circulated over the target board. The rate is generally increased when the temperature of the feedback device is greater than the dynamic temperature set point, and is generally decreased when the temperature of the feedback device is less than the dynamic temperature set point. The rate is generally maintained constant when the temperature of feedback device is substantially equal to the dynamic temperature set point.

Another aspect of the present invention is directed to an accelerated weathering test apparatus of the type used to concentrate solar radiation upon test specimens where the apparatus is adapted to dynamically control a test specimen temperature in accordance with more than one input device. The apparatus includes a target board for supporting at least one test specimen for exposure to concentrated solar radiation. A reflector reflects solar radiation and concentrates the reflected solar radiation on to the target board for illuminating the at least one test specimen. An air circulation device circulates ambient air over the target board for cooling the at least one test specimen. The air circulation device includes an electric motor and a fan powered by the electric motor for creating a flow of ambient air. At least one feedback device is mounted to the target board for exposure to the concentrated solar radiation and each at least one feedback device generates a respective test signal responsive to the temperature thereof and representative of the test specimen temperature. The apparatus further includes at least two input devices which each generates a respective dynamic reference signal. A controller is connected to a first switch for alternatively selecting one of the at least two input devices and is responsive to the selected reference signal for generating a temperature set point. The controller is further connected to a second switch for alternatively selecting one of the at least one feedback device and is responsive to the selected test signal for selectively controlling the application of electrical power to the electric motor, in order to control the rate at which ambient air is circulated over the target board. The rate is generally increased when the temperature of the selected one of the at least one feedback device is greater than the dynamic temperature set point and the rate is generally decreased when the temperature of the one of the at least one feedback device is less than the dynamic temperature set point. The rate is generally maintained when the temperature of the one of the at least one feedback device is substantially equal to the dynamic temperature set point.

Yet another aspect of the present invention is directed to a system for tightly regulating temperature variability between a plurality of accelerated weathering test apparatus of the type used to concentrate solar radiation upon test specimens during an exposure test. The test specimens on each of the plurality of apparatus do not need to be identical. Each apparatus is adapted to dynamically control a test specimen temperature. The system includes the plurality of accelerated weathering test apparatus each including a target board for supporting at least one test specimen to be exposed to concentrated solar radiation. A reflector for reflecting the solar radiation and concentrating the reflected solar radiation onto the target board for illuminating the at least one test specimen. An air circulation device for circulating ambient air over the target board for cooling the at least one test specimen. The air circulation device includes an electric motor and a fan powered by the electrical motor for creating a flow of ambient air. A feedback device sensor is mounted to the target board for exposure to the concentrated solar radiation and generating a test signal responsive to the temperature thereof and representative of the test specimen temperature. An input device for generating a dynamic reference signal representative of a complex temperature cycle of a material end-use application. A controller is connected to the input device and is responsive to the reference signal for generating a dynamic temperature set point. The controller is further connected to the feedback device and is responsive to the test signal for selectively controlling application of electrical power to the electrical motor in order to control the rate at which ambient air is circulated over the target board. The rate is generally increased when the temperature of the feedback device is greater than the dynamic temperature set point and generally decreased when the temperature of the feedback device is less than the dynamic temperature set point. The rate is generally maintained when the temperature of the feedback device is substantially equal to the dynamic temperature set point. The input device of the first one apparatus is disposed remote from the plurality of accelerated weathering test apparatus. The input device of each other apparatus is consecutively linked in series to the first one apparatus such that the other apparatus are dependently controlled from the first one apparatus to reduce temperature variability across the system.

DETAILED DESCRIPTION OF A PREFERRED EMBODIMENT OF THE INVENTION

Figure 1:
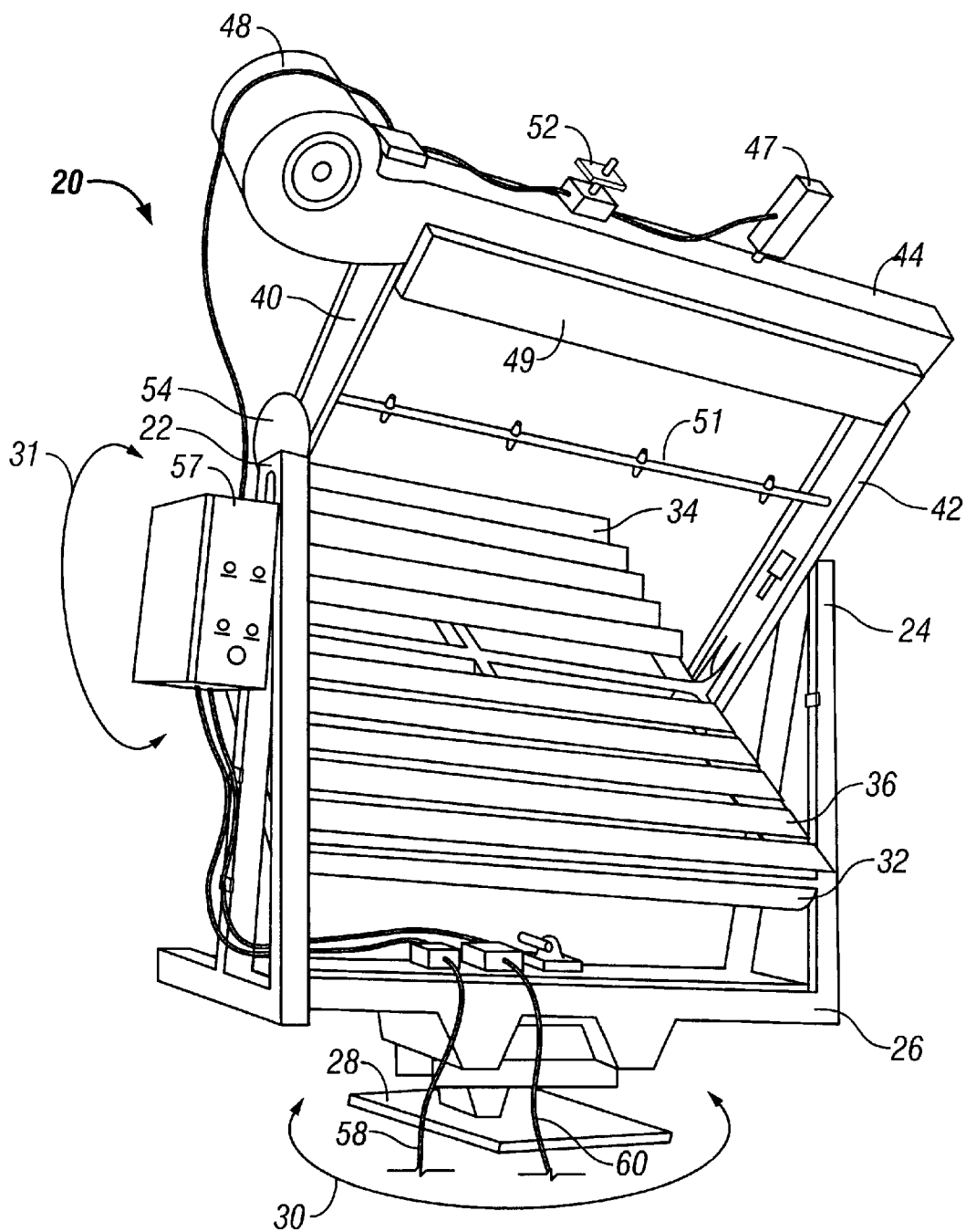
FIG. 1 is a perspective view of a prior art accelerated weathering test apparatus.

Referring to FIG. 1, a prior art accelerated weathering test apparatus is designated generally by reference 20 and includes a pair of A-frame members 22 and 24 to support the operative portion of the apparatus. The lower ends of the A-frame members 22, 24 are interconnected by a base member 26 which is operatively connected to a ground member 28 in order to provide azimuth rotation in the direction indicated by arrow 30 and elevation rotation in the direction indicated by arrow 31. The elevation direction rotation accounts for periodic variation in the sun's altitude at solar noon.

Rotatively supported from the upper ends of A-frame members 22, 24 is a mirror bed frame 32 which supports a plurality of flat mirrors, including those designated by reference numerals 34 and 36. The plurality of mirrors 34, 36 are angled to reflect solar radiation directly impinging upon such mirrors to a target board 38 (see FIG. 2).

Figure 2:
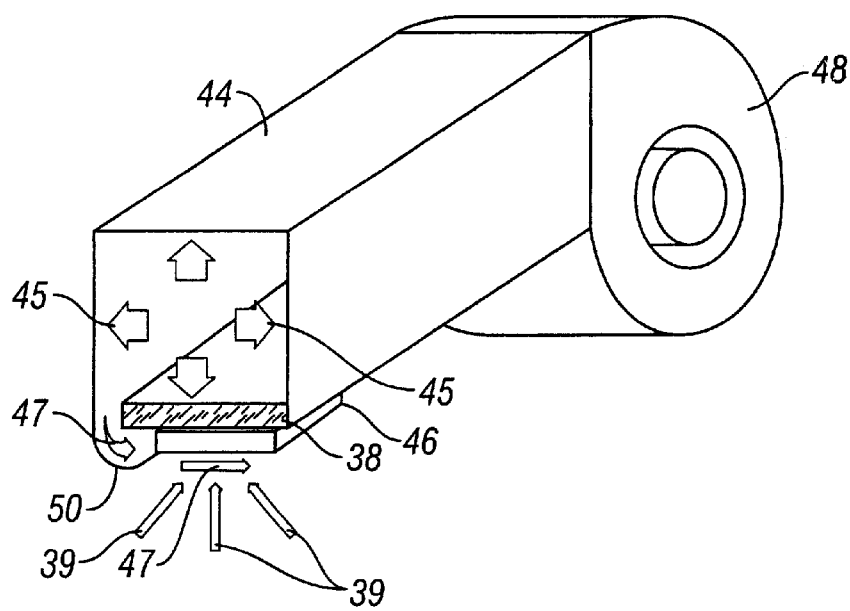
FIG. 2 is a perspective cut-away view of an air circulation device from the accelerated weathering test apparatus of FIG. 1.

A pair of standards 40 and 42 extend outwardly from and perpendicular to mirror bed frame 32. An air tunnel 44 having a generally rectangular cross section is supported by the upper ends of standards 40, 42. Referring to FIG. 2, target board 38 is supported by the lower wall of air tunnel 44, and a plurality of test specimens 46 are mounted to the target board 38 for exposure to the concentrated solar radiation, represented in FIG. 2 by the upwardly extending arrows numbered 39. A squirrel cage blower assembly 48 communicates with one end of the air tunnel 44. Squirrel cage blower assembly 48 includes a fan driven by an electric motor to circulate cooling ambient air through air tunnel 44, represented in FIG. 2 by the outwardly extending arrows numbered 45. As shown in FIG. 2, air tunnel 44 includes a deflector 50 which extends for the length of target board 38 and causes cooling ambient air to be circulated across target board 38 for cooling test specimens 46, represented in FIG. 2 by the arrows numbered 47.

Standards 40, 42 are rotatively supported to upper ends of A-frame members 22, 24. A supporting shaft coincident with the axis of rotation in passing through standards 40, 42 rotably supports that portion of the test apparatus which tracks daily movements of the sun. In order to properly position the Fresnel-reflecting solar concentrator comprised by mirror assembly 34, 36 and reversible electric motor and related gear drive, generally designated by reference number 54, are provided for periodically rotating the mirror bed and target board assembly to track movements of the sun. The clutch preferably couples standard 40 to a shaft to rotate the mirror assembly 34, 36 and target board assembly while permitting manual positioning of the unit at any time to correct for any positioning errors. A solar cell tracking unit 52 controls the application of electrical power to a reversible motor in order to maintain the mirror bed frame 32 perpendicular to incident rays of sunlight. A solar tracker may be of the type which includes two balanced photo cells and a shadowing device mounted above such photo cells for shading them. When an imbalance is detected resulting from one photo cell receiving more sunlight than the other photo cell, an electrical error signal is generated which is amplified and used to apply power to the drive motor 54 for rotating the unit until the photo cells are again balanced, indicating that the unit is properly positioned with respect to the sun.

Also shown in FIG. 1 is a water spray nozzle assembly, designated generally by reference numeral 51. As shown in FIG. 1, spray nozzle assembly 51 is used to periodically spray water at the test specimens to simulate dew, rain, etc.

A hinge shield or cover 49 is shown coupled to the air tunnel 44 opposite the air deflector 50. A door release mechanism 47 is disposed on the air tunnel 44 for engaging and maintaining the shield in a closed position. Upon release, the shield 49 assumes the position shown in FIG. 1 such that concentrated solar radiation reflected by the plurality of mirrors 34, 36 reaches the test specimens 46.

Figure 3:
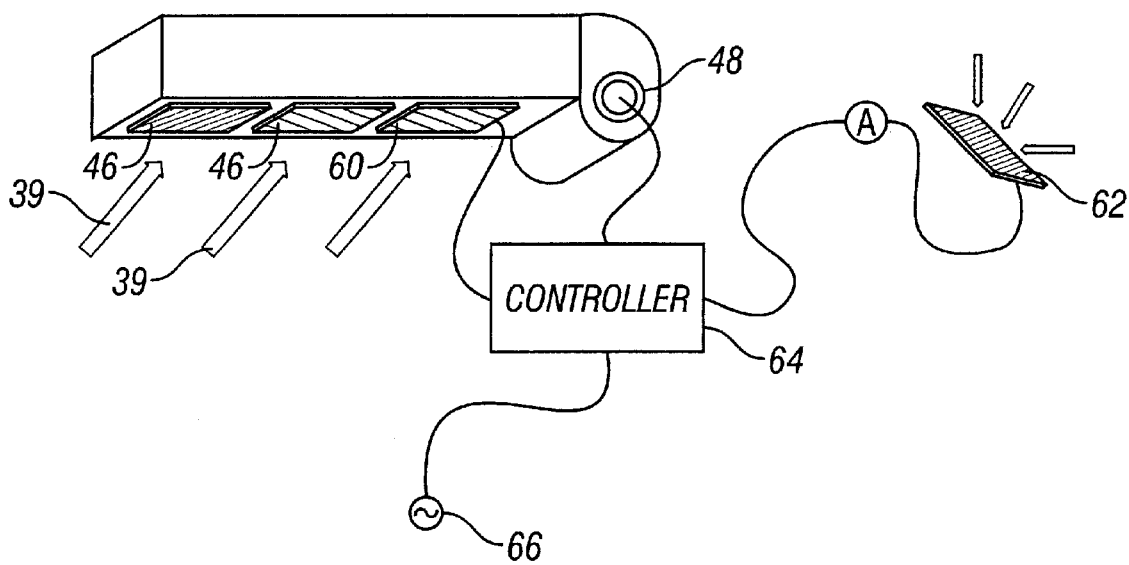
FIG. 3 is a schematic view of the dynamically temperature-controlled accelerated weathering test apparatus in accordance with one embodiment of the present invention.

Referring now to FIGS. 2 and 3, the target board 38 is shown, including at least one test specimen 46 secured thereto. Only one test specimen is shown, however, a plurality are commonly used. Also secured to the target board 38 is a feedback device 60 (FIG. 3) having at least one temperature sensitive component secured in heat conductive relationship therewith. Such component may be a thermistor, thermocouple, resistance temperature device, integrated circuit temperature device or any other suitable device for detecting temperature of the feedback device 60. The feedback device 60 may be formed from a standardized material having known thermal conductive properties or may be formed from a material similar to that of the test specimen. The temperature sensitive component may be embedded within, attached to a back surface or attached to a front surface of the feedback device. Alternatively, a non-contact optical temperature sensing device may be used in order to determine the temperature of the feedback device. The feedback device 60 is preferably coated with black paint to insure that the feedback device 60 will absorb solar radiation impinging upon the area of the target board 38 to which the feedback device 60 is secured. An appropriate black paint which may be used for this purpose is DUPONT DULUX Super Black High Temperature Enamel.

Referring again to FIG. 1, a controller box 57 houses the power and controller systems for the apparatus 20. A power cable 58 supplies electrical power to the apparatus 20 for powering the electric motor 54, which actuates the fan 48. A signal cable 60 is connected to the controller system disposed within the control box 57 for communication with remotely disposed devices, such as the feedback devices and input device, as will be discussed below or for communication with a central command for governing the operation of the apparatus 20 in accordance with the present invention.

Referring to FIG. 3, the schematic illustration shows an embodiment of the present invention for dynamically controlling a test specimen temperature to simulate complex temperature cycles of a material end-use application. As discussed above, the feedback device 60 is mounted to the target board for exposure to the concentrated solar radiation and generating a test signal responsive to the temperature thereof and representative of the test specimen temperature. An input device 62 generates a dynamic reference signal representative of a complex temperature cycle of a material end-use application. A controller 64 is connected to the input device 62 and feedback device 60. The controller 64 is also responsive to the reference signal for generating a dynamic temperature set point. The controller 64 is also responsive to the test signal for selectively controlling application of electric power 66 to the electric motor 48 in order to control a rate at which ambient air is circulated over the target board. The rate is generally increased when the temperature of the feedback device 60 is greater than the dynamic temperature set point and is generally decreased when the temperature of the feedback device 60 is less than the dynamic temperature set point. The rate is generally maintained constant when the temperature of the feedback device 60 is substantially equal to the dynamic temperature set point. In one embodiment of the present invention, controller 64 includes a temperature controller of the type commercially available from Eurotherm Eartrob West Sussex, United Kingdom, under model number 2408 connected to an adjustable alternating current motor speed control of the type commercially available from Boston Fincor of York, Pa., under model number ACX. The aforementioned motor speed control is a solid state, single phase, variable motor speed controller which provides control in proportion to the error sensed between a dynamically adjustable set point determined from the reference signal, as discussed below, and the temperature actually sensed by test sensor 60. The controller 64 includes at least three inputs, a test signal, a reference signal and a power signal. The output of the controller 64 is coupled to one side of the blower motor 48. The opposite of the blower motor 48 is coupled to ground. In one embodiment of the present invention, blower motor 48 is a Graingers Model Number 3805 and the temperature sensing device is preferably a type T thermo couple attached to a test specimen or a standardized black panel.

Other suitable controllers may be used, for example, a processing module including a processor and memory to facilitate management of the operations of the processing module. The processor may be a microprocessor, central processing unit or micro-controller, application-specific integrated circuit, field programmable gate away, a digital signal processor, a micro-controller or any other suitable processing device. If the processor is a microprocessor, it can be a "PENTIUM," "POWER PC," or any other suitable microprocessor, CPU or micro-controller commonly known in the art. The memory may be read-only memory, random access memory, rewritable disc memory, write-once-read-many disc memory, electrically erasable programmable ROM (EEPROM), holographic memory, remote storage memory or any other suitable memory device commonly known in the art. The memory includes instructions that are executed by the processor as well as programming variables or any other suitable programming source code or object code commonly known in the art.

Figure 4A:
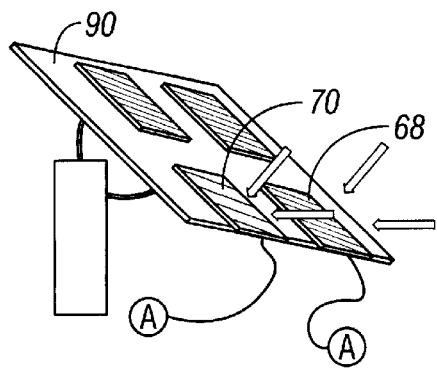
FIGS. 4A–F are representative illustrations of remote devices for dynamically-controlling test specimen temperature in the accelerated weathering test apparatus of FIG. 3.

As discussed above, controller 64 is responsive to the reference signal for generating a dynamic temperature set point. Referring to FIGS. 4A–F, the reference signal may be generated by various different type input devices, each of which detects a complex temperature cycle of a material end-use application. For example, in FIGS. 4A, D and E, a standardized material 68 or a material 70 being tested each having a temperature sensitive component disposed as would be used in such an end-use application as an input device. FIG. 4A illustrates the standardized material 68 or material 70 being tested each disposed on a roof or other similar structure 90. FIG. 4D shows a temperature sensitive component affixed directly to the material being tested or a standardized material disposed on the interior or exterior of an automobile or other similar structure 92. FIG. 4E shows a temperature sensitive component affixed directly to the material being tested or a standardized material disposed on this interior or exterior walls or roof of a building or other similar structure 94.

Figure 4B:
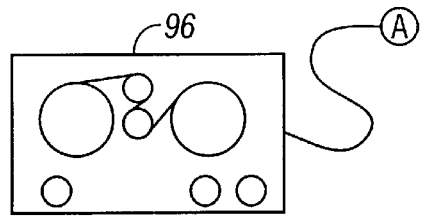
Figure 4C:
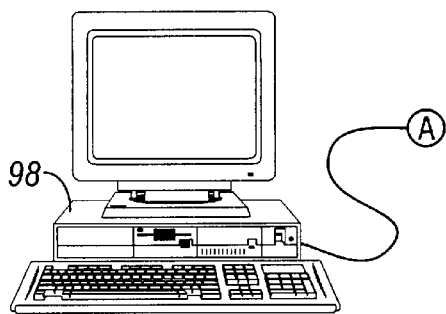
Figure 4D:
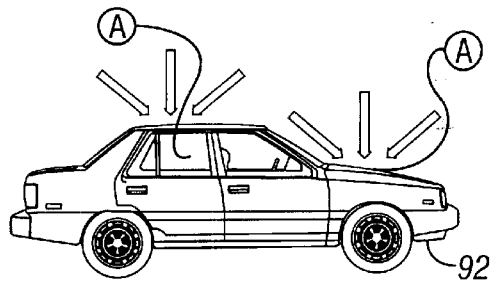
Figure 4E:
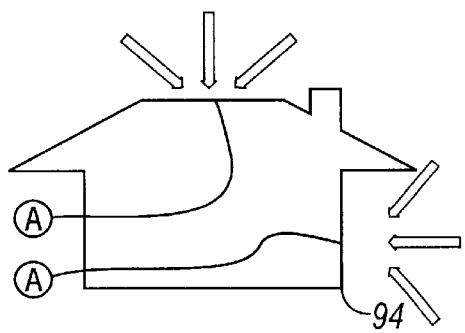
Figure 4F:
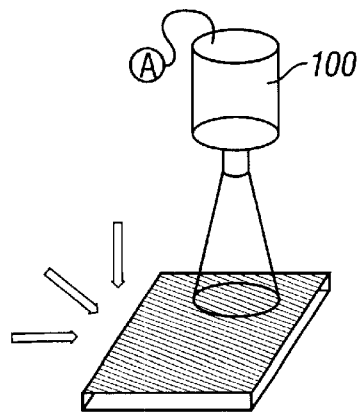

Further, in FIG. 4B, an end-use application environment temperature cycle may be recorded by any conventional manner and replayed such that the apparatus 96 may reproduce the dynamic reference signal of such recorded environment. In FIG. 4C, an apparatus such as a computer 98 may be used for generating a complex temperature cycle as specified by a user to generate the desired reference signal. The computer 98 may also be used for generating a modified version of a recorded end-use application environment temperature cycle to provide environmental temperature elements not commonly observed. A non-contact monitoring device 100, such as an optical infrared pyrometer may be used to generate the reference signal and alternatively the test signal.

The advantage of compatibility with such a wide variety of input devices is that the accelerated weathering test apparatus may be permanently installed in a preferred location, such as, for example, Florida or Arizona, and end-use application environment temperature cycles from any other location may be repeatedly and reproducibly simulated in an exposure test. For example, the input device may be installed on the interior or exterior of an automobile, as shown in FIG. 4D, and the automobile may be either parked at a single location for a specified period of time or moved about within a certain region for a specified period of time. The reference signal may then be recorded, modified or transmitted in real time to the controller in order to generate the dynamic reference signal and corresponding dynamic temperature set point on a periodic basis. In another example, an environment temperature cycle in the Amazon Rain Forest or other critical end-use locations, such as Death Valley for example, may be recorded so that it may be repeatedly and reproducibly simulated at the testing location.

Figure 5:
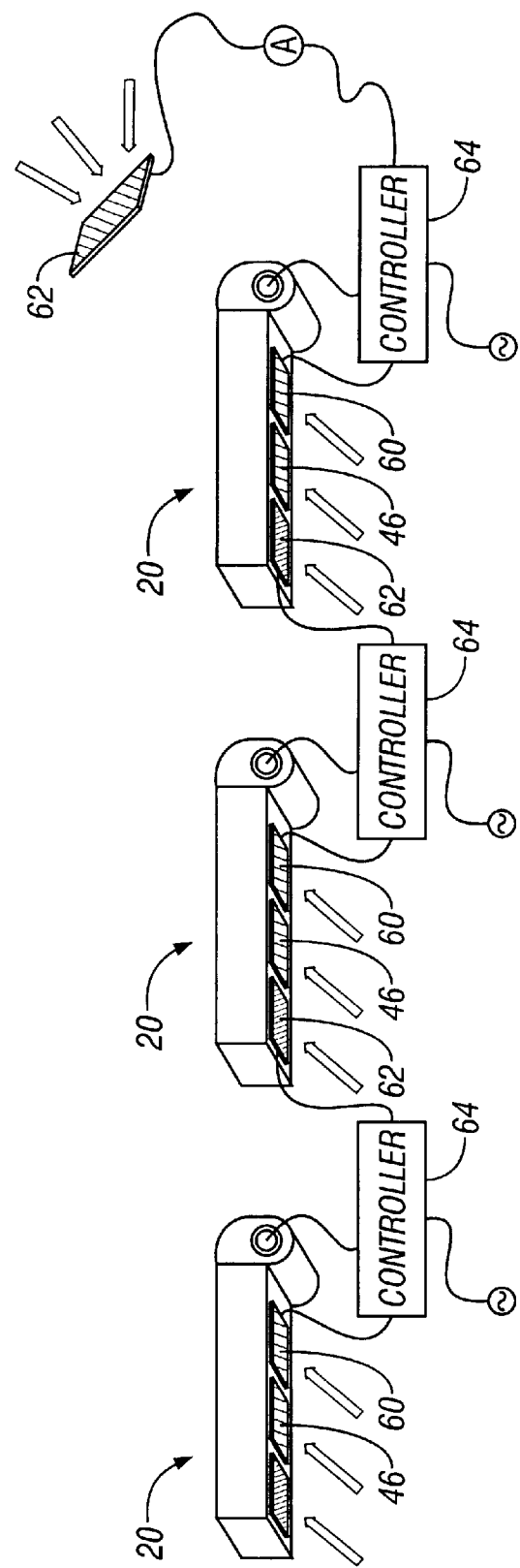
FIG. 5 is a schematic view of a system for regulating temperature variability between a plurality of accelerated weathering test apparatus in accordance with one embodiment of the present invention.

Referring to FIG. 5, in another embodiment of the present invention, a system is illustrated for tightly regulating temperature variability amongst a plurality of accelerated weathering test apparatus 20 of the type used to concentrate solar radiation upon at least one test specimen 46 during an exposure test. The at least one test specimen disposed on each of the plurality of apparatus may be the same. However, a plurality of different test specimens may be used in one exposure test with this system. Thereby, each of the different test specimens is tested under the exact same conditions and all are accordingly tightly regulated. Each apparatus 20 is adapted to dynamically control a test specimen temperature to simulate complex temperature cycles of a material end-use application. The system includes a plurality of accelerated weathering test apparatus 20, as previously described above, including a controller 64, a feedback device 60 and an input device 62. Each of the apparatus 20 operates to dynamically control a test specimen temperature of test specimens mounted thereon to simulate complex temperature cycles of a material end-use application as described above. However, in this embodiment, the plurality of test apparatus 20 are collectively used in one exposure test. A disadvantage of the prior art when attempting an exposure test of this scale, is that the test specimen temperature variance from apparatus to apparatus can be quite large. As a result, any results of the exposure test have a sizable standard deviation. In order to more tightly regulate such standard deviation from apparatus to apparatus, this embodiment of the present invention has the input device 64 of a first one apparatus disposed remote from plurality of accelerated weathering test apparatus 20. The input device 64 of each other apparatus is consecutively linked in series to the first one apparatus such that the other apparatus are dependently controlled therefrom and temperature variably across the system is reduced. This type of arrangement is commonly referred to in the computer networking field as a daisy chain which is defined in Merriam-Webster's Collegiate Dictionary as an interlinked series, much like the links of a chain. This structural configuration, where a second apparatus operates in response to its remote device disposed on a first apparatus, reduces the standard deviation and thereby increases the repeatability or reproducibility of the test results.

Figure 6:
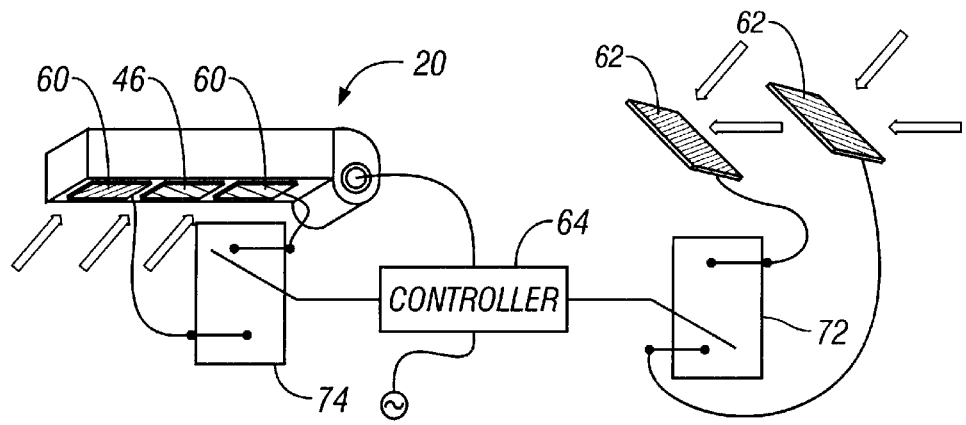
FIG. 6 is a schematic illustration of another accelerated weathering test apparatus in accordance with one embodiment of the present invention.

Referring to FIG. 6, in another embodiment of the present invention, an accelerated weathering test apparatus 20 of the type used to concentrate solar radiation upon test specimens as generally described above, is illustrated. The apparatus 20 is adapted to dynamically control a test specimen temperature to simulate complex temperature cycles of a material end-use application. The general structure of the apparatus 20 has been described in detail above and will be recognized to be the same with respect to this embodiment except for the alternative structure discussed below. The apparatus 20 of this embodiment of the present invention includes at least one feedback device 60 mounted to the target board for exposure to the concentrated solar radiation and for generating a test signal responsive to the temperature thereof which is representative of the test specimen temperature. In this embodiment illustrated in FIG. 6, a pair of input devices 62, in accordance with structure and function previously described above, are shown. At least two input devices 62, each for generating a respective dynamic reference signal representative of a different complex temperature cycle of an end-use application of the test specimen, are shown in this embodiment of the present invention. The controller 64 is connected to a first switch 72 for alternatively selecting one of the at least two input devices 62. This structural configuration allows the apparatus 20 to operate more than one exposure test at a time on a given apparatus 20. Thereby, the test specimens 46 may be exposed to a first temperature cycle for a desired period of time and then a second temperature cycle for a second period of time. It will be recognized by one of skill in the art that specific exposure requirements may be obtained by using this switch in configuration. As discussed above, the controller 64 is responsive to the selected dynamic reference signal for generating a dynamic temperature set point. The controller 64 is further connected to a second switch 74 for alternatively selecting one of the at least one feedback devices 60. In such a configuration, simulated accelerated material degradation can be studied in several different environments, such as, a car component driving back and forth between different environments. Accordingly, service life prediction is more accurate because degradation is a function of the different environments. For example, this embodiment of the present invention may be used to simulate the degradation effects on a material used in an airplane. The temperature and UV values will be different whether on the tarmac or at a thirty thousand foot cruising altitude. Similarly, planes move from location to location about the country and world for that matter. Each different location where the plane visits may be simulated with this embodiment of the present invention. The controller 64 is responsive to the selected test signal for selectively controlling the application of electrical power to the electric motor in order to control the rate at which ambient air is circulated over the target board as discussed above.

Referring to FIGS. 7A–D, in another embodiment of the present invention, in apparatus 20 as described above with respect to FIG. 3, further includes a trimming offset device 76 connected to the controller 64 and the input device 62 for applying an offset to the reference signal. The offset applied to the reference signal may be an absolute offset of a desired amount, a proportional offset in a desired proportion, a function offset, where a desired function is applied to the reference signal or no offset. The advantage of applying an offset to the reference signal is the adjustability a user can apply to an exposure test. This embodiment of the present invention has the additional advantage of adjusting the acceleration rate by allowing more heat and will still include the dynamic cycle nature of the temperature from the input reference signal.

Figure 7A:
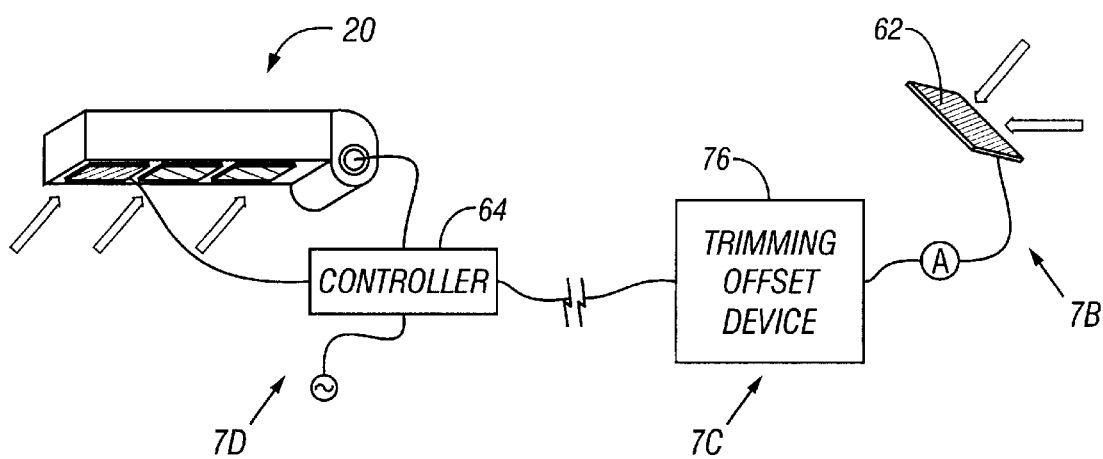
FIG. 7A is a schematic illustration of the accelerated weathering test apparatus depicted in FIG. 3 further including a trimming offset device.
Figure 7B:
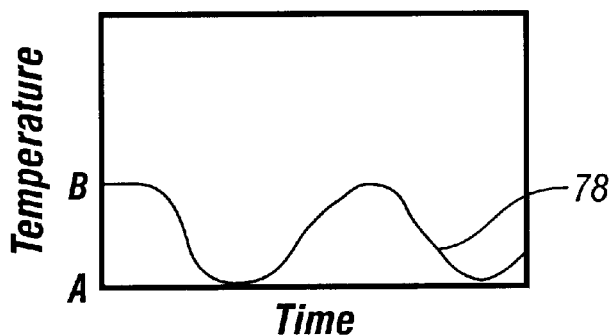
FIGS. 7B–D are graphical representation of a reference signal generated by a remote device to which an offset is applied resulting in a dynamic temperature set point.
Figure 7C:
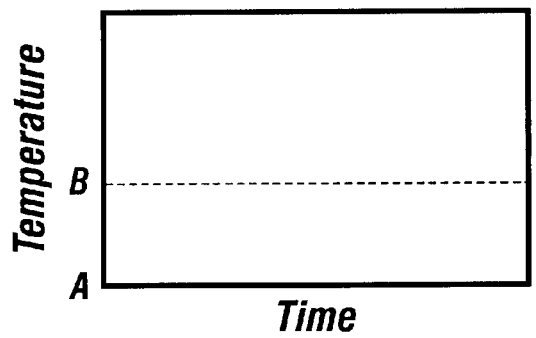
Figure 7D:
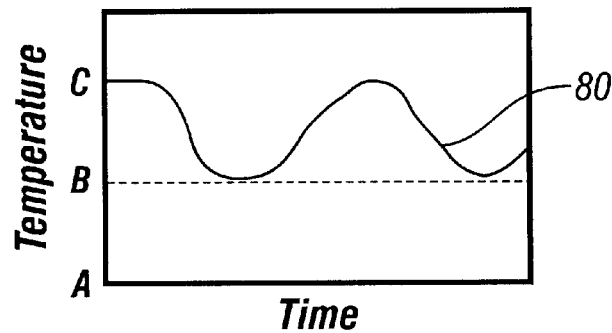

FIG. 7B illustrates a representation trace 78 which oscillates between temperature A and temperature B over a period of time. This trace 78 is representative of the reference signal at location 7B in FIG. 7A. FIG. 7C illustrates the function of the trimming offset device 76 at location 7C in FIG. 7A where an absolute offset is applied raising the base line from temperature A to temperature B. FIG. 7D illustrates a representative trace 80 to which the absolute offset was applied and is representative of the test signal observed by the controller 64 at location 7D in FIG. 7A.

While the invention has been described with reference to a preferred embodiment thereof, the description is for illustrative purposes only and is not to be construed as limiting the scope of the invention. Various modifications and changes may be made by those skilled in the art without departing from the true spirit and scope of the invention as defined by the dependent claims. For example, mechanical or optical control devices may be substituted for the control and input signals and that other methods to effect temperature using the mirrors rather than the blown air may be used. For instance, defocusing mirrors instead of changing the blowers speed may provide the same results. Additionally, a damper or mechanical valve in the air tunnel may be used to change the amount of cooling air circulated over the test specimen. Finally, filters (polarizing, interference, tunable, etc.) may be used to effect the radiance and the temperature.

What is claimed is:

1. An accelerated weathering test apparatus of the type used to concentrate solar radiation upon test specimens, the apparatus dynamically controlling a test specimen temperature in order to simulate complex temperature cycles of a material end-use application, the apparatus comprising:

a target board for supporting at least one test specimen to be exposed to concentrated solar radiation;

a reflector device for reflecting solar radiation and concentrating the reflected solar radiation on to the target board for illuminating the at least one test specimen;

an air circulation device for circulating ambient air over the target board for adjusting the temperature of the at least one test specimen, the air circulation device including an electric motor and a fan powered by the electric motor for creating a flow of ambient air;

a feedback device mounted to the target board for exposure to the concentrated solar radiation and generating a test signal responsive to a temperature thereof and representative of the test specimen temperature;

an input device which continuously generates a dynamic reference signal representative of a complex temperature cycle of a material end-use application; and a controller connected to the input device and responsive to the dynamic reference signal in order to generate a temperature set point, and the controller further connected to the feedback device and responsive to the test signal for selectively controlling the application of electrical power to the electric motor in order to control a rate at which ambient air is circulated over the target board, the rate being generally increased when the temperature of the feedback device is greater than the temperature set point, and the rate being generally decreased when the temperature of the feedback device is less than the temperature set point, and the rate being generally maintained constant when the temperature of feedback device is substantially equal to the temperature set point.

2. The apparatus cited by claim 1, wherein the input device is a temperature sensitive component, an apparatus for replaying a recorded environment temperature cycle, an apparatus for generating a complex temperature cycle or a non-contact monitoring device.

3. The apparatus recited by claim 1, wherein the apparatus further includes a trimming offset device connected to the controller and the input device for applying an offset to the reference signal.

4. The apparatus recited by claim 3, wherein the offset applied to the reference signal is an absolute offset, a proportional offset, a function offset or no offset.

5. The apparatus recited by claim 1, wherein the fan is a squirrel cage blower powered by the electric motor.

6. The apparatus recited by claim 1, wherein the air circulation device includes an air tunnel coupled to the target board, the air tunnel having an outlet extending coextensive with the target board for circulating ambient air over the target board.

7. The apparatus recited by claim 1, wherein the feedback device is secured in a heat conductive relationship to a panel mounted to the target board.

8. The apparatus recited by claim 7, wherein the feedback device further includes a black coating overlying the feedback device and the panel for absorbing solar radiation impinging thereon.

9. An accelerated weathering test apparatus of the type used to concentrate solar radiation upon test specimens, the apparatus being adapted to dynamically control a test specimen temperature to simulate complex temperature cycles of a material end-use application, the apparatus comprising:

a target board for supporting at least one test specimen to be exposed to concentrated solar radiation;

a reflector device for reflecting solar radiation and concentrating the reflected solar radiation on to the target board for illuminating the at least one test specimen;

an air circulation device for circulating ambient air over the target board for cooling the at least one test specimen, the air circulation device including an electric motor and a fan powered by the electric motor for creating a flow of ambient air;

at least one feedback device mounted to the target board for exposure to the concentrated solar radiation and generating a test signal responsive to the temperature thereof and representative of the test specimen temperature;

at least two input devices, each for generating a respective dynamic reference signal representative of a different complex temperature cycle of a material end-use application; and a controller connected to a first switch for alternatively selecting one of the at least two input devices and responsive to the selected dynamic reference signal for generating a temperature set point, and the controller further connected to a second switch for alternatively selecting one of the at least one feedback device and responsive to the selected test signal for selectively controlling the application of electrical power to the electric motor in order to control a rate at which ambient air is circulated over the target board, the rate being generally increased when the temperature of the selected one of the at least one feedback device is greater than the temperature set point, and the rate being generally decreased when the temperature of the one of the at least one feedback device is less than the temperature set point, and the rate being generally maintained constant when the temperature of the one of the at least one feedback device is substantially equal to the temperature set point.

10. The apparatus cited by claim 9, wherein the input device is a temperature sensitive component, an apparatus for replaying a recorded environment temperature cycle, an apparatus for generating a complex temperature cycle or a non-contact monitoring device.

11. The apparatus recited by claim 9, wherein the apparatus further includes a trimming offset device connected to the controller and the first switch for applying an offset to the selected reference signal.

12. The apparatus recited by claim 11, wherein the offset applied to the reference signal is an absolute offset, a proportional offset, a function offset or no offset.

13. The apparatus recited by claim 9, wherein the fan is a squirrel cage blower powered by the electric motor.

14. The apparatus recited by claim 9, wherein the air circulation apparatus device includes an air tunnel coupled to the target board, the air tunnel having an outlet extending coextensive with the target board for circulating ambient air over the target board.

15. The apparatus recited by claim 9, wherein the feedback device is secured in a heat conductive relationship to a panel mounted to the target board.

16. The apparatus recited by claim 15, wherein the feedback device further includes a black coating overlying the feedback device and the panel for absorbing solar radiation impinging thereon.

17. The apparatus recited by claim 9, wherein the controller selects one of the at least one feedback device which is operatively compatible with the selected one of the at least two input devices.

18. A system for tightly regulating temperature variability amongst a plurality of accelerated weathering test apparatus, of the type used to concentrate solar radiation upon at least one test specimen, during an exposure test where each apparatus is adapted to dynamically control a test specimen temperature to simulate complex temperature cycles of a material end-use application, the system comprising:

each of the plurality of accelerated weathering test apparatus including:
  a target board for supporting the at least one test specimen to be exposed to concentrated solar radiation;
  a reflector for reflecting solar radiation and concentrating the reflected solar radiation onto the target board for illuminating the at least one test specimen;
  an air circulation device for circulating ambient air over the target board for cooling the at least one test specimen, the air circulation device including an electric motor and a fan powered by the electrical motor for creating a flow of ambient air;
  a feedback device mounted to the target board for exposure to the concentrated solar radiation and generating a test signal responsive to the temperature thereof and representative of the test specimen temperature;
  an input device for continuously generating a dynamic reference signal representative of a complex temperature cycle of a material end-use application; and
  a controller connected to the input device and responsive to the reference signal for generating a temperature set point, and the controller further connected to the feedback device and responsive to the test signal for selectively controlling application of electrical power to the electric motor, in order to control a rate at which ambient air is circulated over the target board, the rate being generally increased when the temperature of the feedback device is greater than the dynamic temperature set point, and the rate being generally decreased when the temperature of the feedback device is less than the dynamic temperature set point, and the rate being generally maintained constant when the temperature of the feedback device is substantially equal to the dynamic temperature set point;

the input device of a first one apparatus disposed remote from the plurality of accelerated weathering test apparatus; and the input device of each other apparatus consecutively linking in series the first one apparatus and the other apparatus, such that the other apparatus are dependently controlled from the first one apparatus to reduce temperature variability across the system.

19. The system cited by claim 18, wherein the input device associated with the first one apparatus is a temperature sensitive component, an apparatus for replaying a recorded environment temperature cycle, an apparatus for generating a complex temperature cycle or a non-contact monitoring device.

20. The system recited by claim 18, wherein the first one apparatus further includes a trimming offset device connected to the controller and the input device for applying an offset to the reference signal.

21. The system recited by claim 20, wherein the offset applied to the reference signal is an absolute offset, a proportional offset, a function offset or no offset.

22. The system recited by claim 18, wherein the fan is a squirrel cage blower powered by the electric motor.

23. The system recited by claim 18, wherein the air circulation device includes an air tunnel coupled to the target board, the air tunnel having an outlet extending coextensive with the target board for circulating ambient air over the target board.

24. The system recited by claim 18, wherein the feedback device is secured in a heat conductive relationship to a panel mounted to the target board.

25. The system recited by claim 24, wherein the feedback device further includes a black coating overlying the feedback device and the panel for absorbing solar radiation impinging thereon.

26. The system recited by claim 24, wherein the input device associated with the other apparatus is a temperature sensitive component or a non-contact monitoring device.

* * * * *

UNITED STATES PATENT AND TRADEMARK OFFICE
CERTIFICATE OF CORRECTION

PATENT NO.    : 6,659,638 B1
DATED         : December 9, 2003
INVENTOR(S)   : Henry K. Hardcastle, III It is certified that error appears in the above-identified patent and that said Letters Patent is hereby corrected as shown below:

<u>Title page,</u>
Item [12], should read

-- [12] United States Patent
        Hardcastle, III --

Item [75], Inventor, should read

-- [75] Inventor: Henry K. Hardcastle, III, Sunrise, FL (US) --

Signed and Sealed this

Fourth Day of May, 2004

JON W. DUDAS
*Acting Director of the United States Patent and Trademark Office*